United States Patent [19]

Olsen

[11] 4,144,644
[45] Mar. 20, 1979

[54] MODULAR SELECTOR VALVE ASSEMBLY

[75] Inventor: Robert A. Olsen, Palatine, Ill.

[73] Assignee: American Hospital Supply Corporation, Evanston, Ill.

[21] Appl. No.: 697,201

[22] Filed: Jun. 17, 1976

[51] Int. Cl.² .............................................. A61C 19/02
[52] U.S. Cl. ...................................................... 32/22
[58] Field of Search ................................ 32/22, 26, 27

[56] References Cited

U.S. PATENT DOCUMENTS 3,918,161  11/1975  Morgan ..................................... 32/22

FOREIGN PATENT DOCUMENTS 2339824  8/1973  Fed. Rep. of Germany .............. 32/22

Primary Examiner—Robert Peshock
Attorney, Agent, or Firm—Tilton, Fallon, Lungmus & Chestnut

[57] ABSTRACT

A modular multi-function selector valve assembly for controlling the flow of fluids for a plurality of dental handpieces. Each of the modules is functionally associated with one of such handpieces and, in response to the absence or presence of pilot air pressure, the multiple valves of that module simultaneously open or close passages for drive air, chip air, and water, as well as for other fluids such as exhaust air and gauge air. The modules are disposed in side-by-side relation with each other and each module is transversely divided into control and valve sections. A plurality of main and secondary flow passages are formed in the sections, and one side of each section is also provided with at least one channel communicating with certain of such passages. Flexible gaskets, interposed between adjacent modules and also between respective sections of each module, perform the multiple functions of preventing leakage from the main and secondary passages, combining with the channels to define additional flow passages, and serving as diaphragm valves for controlling fluid flow. In the embodiment disclosed, the module sections, along with their passages and cnannels, are formed by injection molding, the flexible gaskets between such sections and between successive modules are all identical, and the clamping plates which are used to secure the modules in side-by-side relation are identical but reversely oriented relative to each other.

11 Claims, 6 Drawing Figures

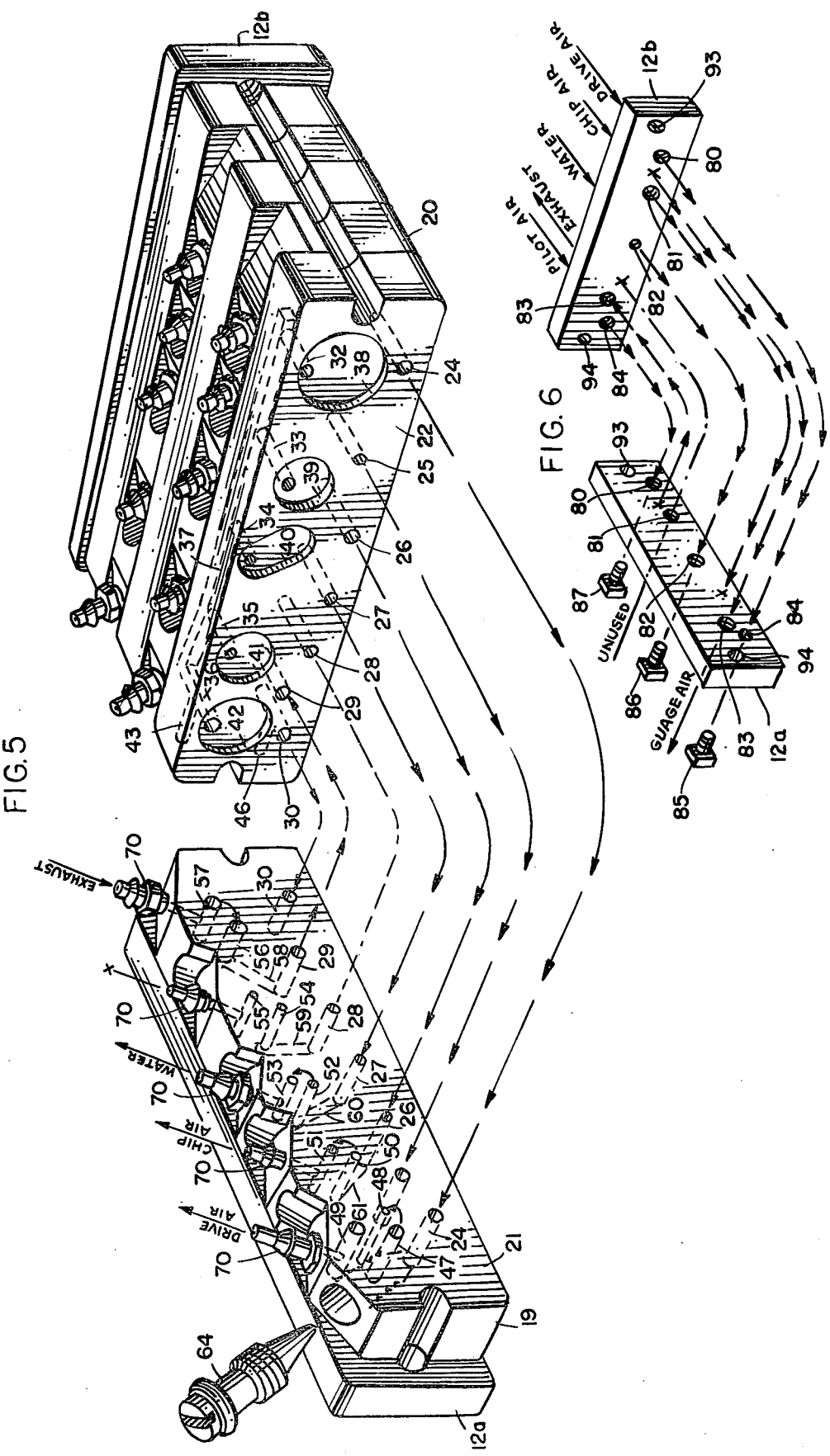

MODULAR SELECTOR VALVE ASSEMBLY

BACKGROUND

Selector valve assemblies are well known for use with dental handpieces as disclosed, for example, in U.S. Pat. No. 3,446,749. Such a selector valve serves to make drive air, chip air, and water available to the particular dental handpiece selected for use by a dentist while at the same time preventing the flow of such fluids to the handpieces which have not been selected for use and which remain supported by the sockets or hangers of the dental console. Each selector valve of the group is controlled by a pilot valve associated directly with a handpiece hanger; when such a handpiece is lifted from its hanger for use by the dentist, the pilot valve is operated to cause all of the valves (for drive air, chip air, water, exhaust air, etc.) of the associated selector valve to open. Final selection and regulation of the fluids to the selected handpiece is achieved by a standard foot controller operated by the dentist's foot but, until the selector valve for the particular handpiece is actuated by its pilot valve (which in turn is actuated by removal of the handpiece from its hanger), the handpiece remains inoperative.

Since a typical selector valve assembly functions to control fluid flow for a plurality of handpieces (normally three or more), and since each handpiece is supplied with drive air, chip air, and water requiring separate passages and valves, the usual selector valve is relatively bulky, intricate, and expensive. Ordinarily, the passages in a selector valve module are formed by mutliple drilling and machining operations. While the complexity of such a valve assembly is reduced somewhat by substituting diaphragm valves for piston valves (as in U.S. Pat. No. Re. 28,649), production of the modified structure nevertheless requires a substantial number of different parts and a variety of expensive machining, drilling, and assembly operations.

Other references disclosing the state of the art are U.S. Pat. Nos. 3,469,582, 3,022,039, 3,083,943, and 3,286,977.

SUMMARY OF THE INVENTION

A main aspect of this invention lies in providing an improved selector valve assembly composed of a limited number of parts which may be easily formed by injection-molding and die-cutting operations and which may be easily assembled to provide a modular structure of any desired size depending on the number of dental handpieces with which it is to be used. The result is a compact valve assembly which is relatively simple and inexpensive to manufacture.

In the improved selector valve assembly, a series of substantially identical modules are secured together in side-by-side relation. Each module has a pair of parallel planar outer side faces and is divided along a plane parallel with those faces into a valve section and a control section. An arrangement of main flow passages extends through the sections of each module from one side face to the other with the passages of one module being in axial alignment with corresponding passages of the next. In addition to the main passages which are common to both the control and valve sections of each module, such sections are also provided with their own distinctive secondary passages which are parallel to the main passages. Since all of such passages are perpendicular to the planar side faces of the module sections, such passages may be readily formed by injection molding procedures in contrast to drilling operations.

The outer side faces of the two sections are also provided with channels which extend between certain of the secondary passages. When the parts are later assembled with gaskets between the sections of each module and between successive modules of the group, the intermodular gaskets close the sides of the channels to form connecting passageways between the secondary passages of the sections. Such intermodular gaskets also perform the function of sealing the modules against leakage from their communicating main passages and from their distinctive secondary passages.

The intramodular gaskets perform the usual sealing function and, in addition, constitute flexible diaphragm valves for controlling fluid flow in response to pilot air pressure. In the embodiment disclosed, the intramodular gaskets are identical to the intermodular gaskets — a cost-saving feature which also facilitates repair or replacement and reduces the required inventory of parts.

The modules and their sections are all clamped between a pair of rigid clamping plates. Cost saving is again achieved by making the clamping plates identical to each other. Although identical, the plates preferably have some openings which are not symetrically arranged, the result being that the openings of one plate communicate directly with certain main passages extending through the assembly while the openings of the other plate (which is identical in configuration but oppositely-oriented) communicate with other main passages.

Other objects and advantages of the invention will become apparent from the specification and drawings.

DRAWINGS

FIG. 5 is a perspective view of a selector valve assembly with the sections of one module separated from each other, and with the gasket normally therebetween removed from view, to illustrate the relationship of parts.

FIG. 6 is a reduced perspective view showing only the end plates (and plugs) in the same relationship depicted in FIG. 5.

DETAILED DESCRIPTION

Figure 1:
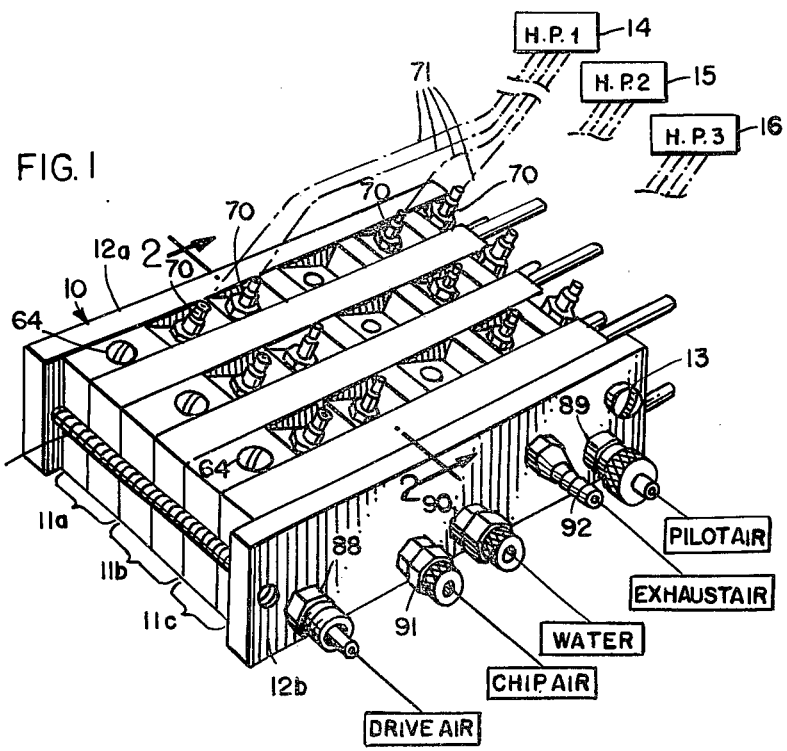
FIG. 1 is a perspective view of a selector valve embodying the present invention.

In the embodiment illustrated in the drawings, the numeral 10 generally designates a selector valve assembly comprising three substantially identical modules 11a, 11b, and 11c between a pair of clamping plates 12a and 12b. One or more screws 13 extend between the plates to hold them in tight clamping relation with respect to the modules. While three modules are shown, a greater or smaller number may be provided depending upon the number of handpieces involved. Three such handpieces 14–16 are diagrammatically illustrated in FIG. 1; since such handpieces are entirely conventional, and since their construction and operation are well known, a more detailed description is believed unnecessary. Reference may be had to U.S. Pat. Nos. Re. 28,390 and 3,386,702 for information on air driven dental handpieces of the type now well known in the art. Further reference may be had to aforementioned U.S. Pat. Nos. 3,466,749 and Re. 28,649 for the general relationship between handpieces, hanger pilot valves, foot control valves, and selector valves as known in the art.

Figure 2:
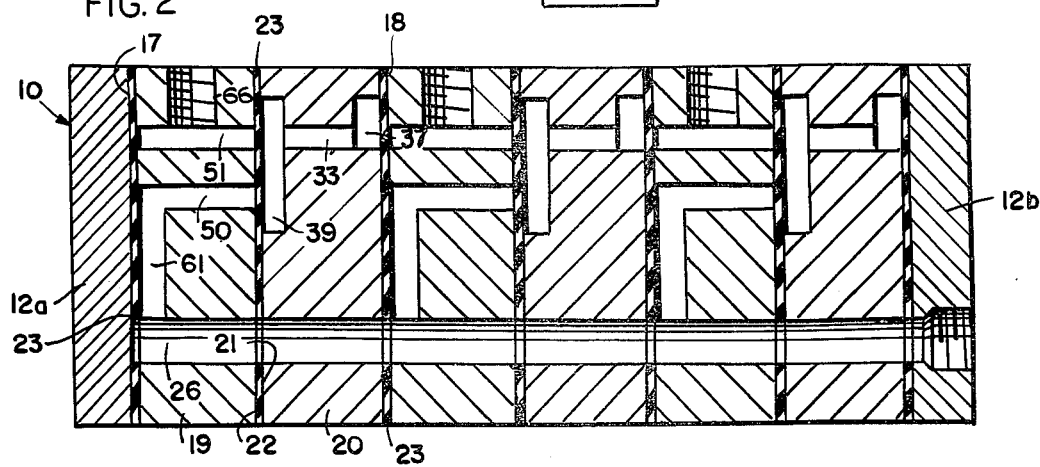
FIG. 2 is an enlarged cross sectional view taken along line 2—2 of FIG. 1.

The selector valve assembly 10 is generally rectangular in configuration, as are all of the modules of which it is composed. Each module has a pair of parallel planar outer side faces 17 and 18 and is transversely divided into a valve section 19 and a control section 20 (FIG. 2). The inner opposing side faces 21 and 22 of the respective sections are separated by a flexible gasket 23. Identical gaskets are also interposed between the outer side faces of successive modules, or between the outer side face of a module and an end plate.

Figure 4:
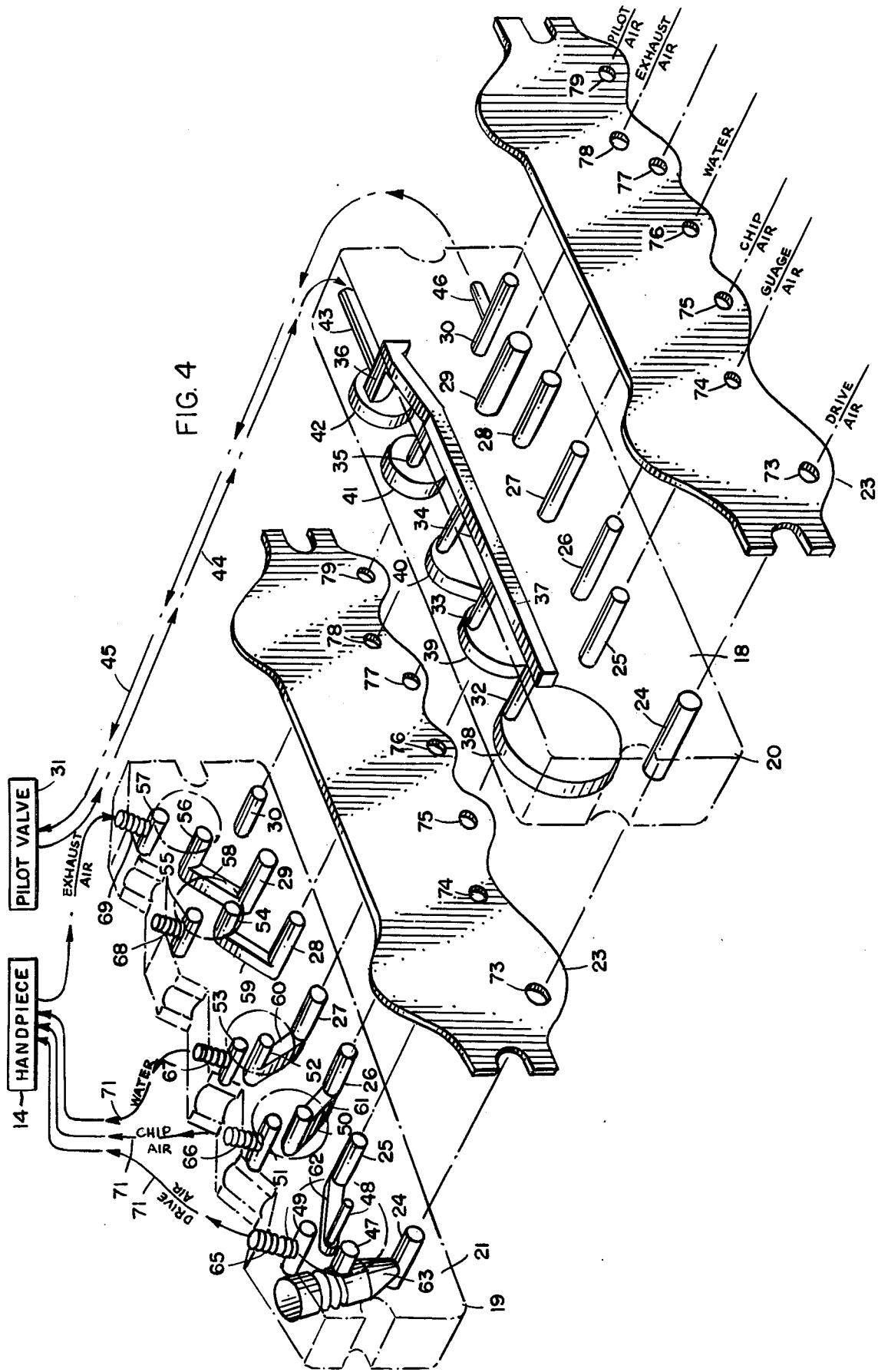
FIG. 4 is an exploded perspective view of the components of a single module with the passages and openings illustrated in solid lines and the outlines of the parts shown in phantom.

FIG. 4 illustrates the basic components of a module in exploded relation, the parts being illustrated in phantom lines and their passages being represented by solid lines to depict more clearly the functional relationship of such parts. It will be observed that each section has an arrangement of transversely-extending main flow passages 24–30 with corresponding passages of the two sections being in axial alignment. Similarly, corresponding passages of successive modules are also disposed in axial alignment. In the embodiment illustrated, passage 24 is intended to carry drive air, that is, air under pressure (ordinarily about 35 psig) for operating the turbine of an air-driven dental handpiece. Passage 25 carries gauge air and communicates with a suitable air pressure gauge (not shown) for advising the dentist of the pressure of the drive air supplied to the handpiece. Passage 26 carries chip air which may be discharged at the head of the handpiece, either with or without water supplied through passage 27, to cool the bur (and tooth) and flush away debris developed during a cutting or polishing operation. Passage 29 conducts return or exhaust air from those handpieces which do not discharge to atmosphere all of the air passing through the turbine, and passage 30 carries pilot air to be directed to the pilot valve 31 associated with the supporting hanger or socket (not shown) for each handpiece. Passage 28 is an auxiliary passage which, in the form shown, is not used at all but may, if desired, be utilized to provide additional air (or other fluid) to the handpieces for other selected functions. All of the main passages 24–30 are parallel with each other, all pass completely through the sections 19 and 20 of each module, and all constitute segments of passages common to all of the modules.

Each of the paired sections 19 and 20 is also provided with transverse secondary passages which are distinctive to that particular section and do not appear in the other section of the pair. Thus, control section or block 20 has transverse control passages 32–36 as shown in FIGS. 4 and 5. All of the control passages are parallel to each other and extend completely through control section 20. Along its outer side face the control section 20 is provided with an elongated open-sided connecting channel 37 which joins all of the transverse valve passages 32–36. The opposite inner face 22 has a plurality of indentations or recesses 38–42 which communicate with the respective control passages 32–36 and which, in combination with flexible gasket 23, define variable volume chambers for receiving pilot air. When the parts are assembled, the gasket 23 against the outer face 18 of control section 20 extends along the full length of channel 37, closing the otherwise-open side of the channel so that the channel becomes a manifold for directing pilot air to and from each of the recesses or chambers 38–42. The pilot air is available to the manifold channel by means of end passage 42 which communicates directly with a pilot air line represented in FIG. 4 by arrows 44. The line 44 extends to pilot valve 31 which is in turn supplied with pressurized air from a supply line represented by arrows 45. The supply line connects with end passage 46 which extends into the main transverse passage 30 (of control section 20) for conveying pilot air through the modules (FIG. 4).

The valve section 19 of each module is provided with a plurality of transverse secondary passages 47–57. All of such transverse valve passages are parallel to each other and extend completely through the valve block or valve section 19. It will be observed from FIGS. 4 and 5 that such transverse passages are arranged in pairs. Passages 47 and 49 constitute such a pair used for the flow of drive air. Passages 50 and 51 convey chip air, passages 52 and 53 conduct water, and passages 56 and 57 carry exhaust air. Passages 54 and 55 are auxiliary passages which may be used to carry any desired fluid and, as in the embodiment illustrated, may not be used at all.

One transverse passage of each pair communicates with one of the main flow passages 24–30, in most instances by means of connecting channels formed in the outer side surface 17 of the valve section. Accordingly, a connecting channel 58 bridges secondary passage 56 and primary passage 29 (for exhaust air), connecting channel 59 extends between secondary passage 54 and primary auxiliary passage 28, connecting channel 60 bridges secondary passage 52 and primary passage 27 (for water), channel 61 extends between secondary passage 50 and primary passage 26 (chip air), and channel 62 extends between secondary passage 48 and primary passage 25 (for gauge air). An internally threaded bore 63 extends between secondary passage 47 and primary drive air passage 24 and receives a needle valve member 64 (FIGS. 4 and 5).

All of the communicating channels 58–62 of the valve section 19 are open-sided; that is, they are open along the outer side surface 17 of that section. Like the open side of previously-described channel 37, however, the open sides of connecting channels 58–62 are closed by a gasket 23 which extends along the outer side surface 17 of module section 19. The relationship is clearly illustrated in FIG. 2 where it will be seen that the connecting channel 61 which extends between the main transverse passage 26 for chip air and the secondary transverse passage 50 is closed along its left side by gasket 23. The gasket thereby contributes in converting the open channel into a passage for the flow of chip air.

The upper secondary passages 49–57 of each pair are joined by bores 65–69, respectively, which extend to the top of the valve section 19 and which are threaded or otherwise adapted to receive fittings 70 as depicted in FIGS. 1 and 5. Tubes 71 extend from the connectors for conveying fluids such as drive air, chip air, and water to a dental handpiece.

Each gasket 23 is formed of rubber or other flexible sheet material and is provided along its lower portion with a series of openings 73–79, all of which register with the main flow passages 24–30 which extend transversely through the sections of the modules. In the embodiment illustrated, all of the gaskets are identical but their functions differ depending on whether they are used between successive modules (as intermodular gaskets) or between sections of the same module (as intramodular gaskets). Referring to FIG. 4, the lower gasket is an intermodular gasket and is disposed between outer surface 18 of one module and the outer surface 17 of the next module. As already described, such a gasket not only performs a normal gasket function of preventing leakage between the main flow passages 24–30 of adjacent modules but also defines side walls for converting connecting channels 37 and 58–62 into closed flow passages.

Figure 3:
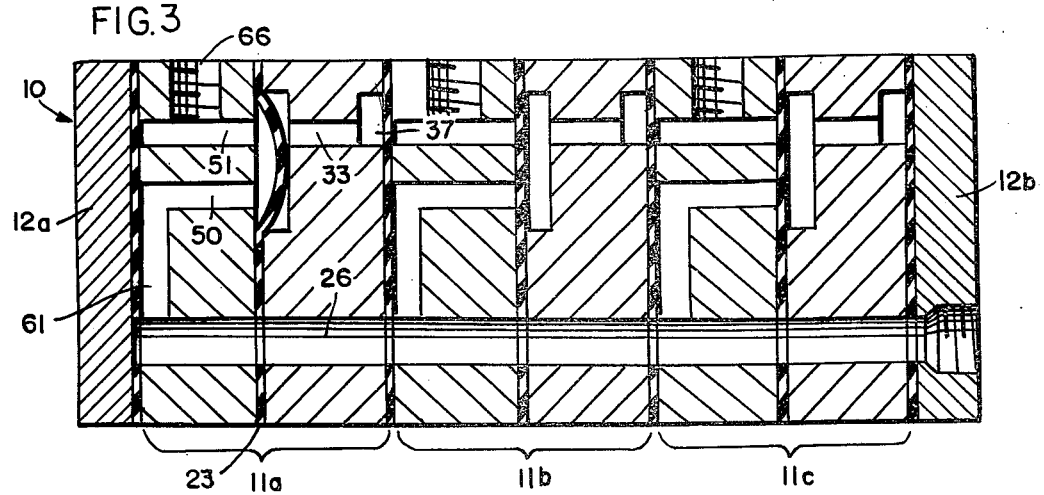
FIG. 3 is a sectional view similar to FIG. 2 but illustrating one of the modules with its pilot-operated valves in open position.

Each intramodular gasket similarly prevents leakage from the main transverse flow passages 24–30. However, unlike the intermodular gaskets, the intramodular gaskets also perform a valving function. That function is depicted most clearly in FIGS. 2 and 3 where it will be seen that when chamber 39 is pressurized with pilot air supplied through mainifold 37 and secondary passage 33 the imperforate upper portion of the intramodular gasket seals the openings of secondary passages 50 and 51 in valve section 19, thereby preventing flow of chip air from passage 50 to passage 51. FIG. 2 therefore illustrates the normal closed condition of the selector valves, such condition arising because the normally open pilot valve 31 permits air under pressure to flow from main pilot air passage 30 through tubes 45 and 44, and then through passages 43 and 37 to each of the chambers 38–42. When the pilot valve associated with a selected handpiece is closed, by simply lifting that handpiece from the hanger or socket in which it is normally supported (see U.S. Pat. Nos. 3,466,749 and Re. 28,649), the chambers are depressurized and drive air, chip air, water, and exhaust air are free to flow from one secondary passage to the other secondary passage of each pair. For example, in FIG. 3, when chamber 39 is depressurized, the pressure of chip air flowing from main passage 26 through connecting passage 61 and secondary passage 50 causes the flexible gasket or membrane to bow outwardly into the chamber, thereby opening the valve and permitting chip air to flow into secondary passage 51, upstanding passage 66, tube 71 and ultimately to handpiece 14 (FIGS. 3 and 4).

Terminal clamping plates 12a and 12b are identical but are reversely positioned at opposite ends of the modular stack so that the threaded openings 80–84 through each plate register somewhat differently with the primary flow passages 24–30 extending transversely through that stack. The relationship is best illustrated in FIG. 6 where the end plates are shown in the same positions depicted in FIG. 5 but with all other parts except plugs 85–87 omitted. With the end plates so oriented, opening 80 of one plate is in register with opening 84 of the other, and central openings 82 of the respective plates in register with each other. Drive air, pilot air, and water may therefore be introduced through the threaded openings 80, 84, and 82 in one of the plates and will flow through primary passages 24, 30, and 27 of the modules, exiting through openings 84, 80, and 82 of the other terminal plate. Plugs 85–87 prevent the escape of of such fluids through terminal plate 12a. While three such plugs 85–87 are depicted in FIG. 6 in association with plate 12a, it should be understood that the flow of fluid through one or more of the primary passages might be reversed so that a plug or plugs would be associated with plate 12b, and further, that the plugs for certain passages might be omitted entirely. Thus, if pilot air is also to be used for a syringe or other instrument, plug 87 may be omitted entirely and a suitable conduit leading to the syringe may be substituted.

As shown in FIG. 1, suitable fittings 88, 89, and 90 are securely connected by threads or other appropriate means (such as cement, sonic welding, etc.) to the plate 12b and are in direct communication through suitable conduits with sources of drive air, pilot air, and water, all of as diagrammatically illustrated in that figure.

When the clamping plates are reversely oriented as shown in FIG. 6, certain openings 81 and 83 of one plate do not register with any openings of the other plate; however, each such opening does register with a primary flow passage extending through the modular stack. Therefore, the two openings 81 and 83 of the opposing end plates provide four ports (two at each end of the modular assembly) for the entry or discharge of gauge air, chip air, exhaust air, and an auxiliary fluid. More specifically, opening 81 of plate 12b registers with primary flow passage 26 for the flow of chip air into the modular assembly (through fitting 91 shown in FIG. 1), opening 83 in the same plate registers with primary passage 29 for the escape of exhaust air from the modular assembly (through fitting 92 shown in FIG. 1), opening 81 in plate 12a registers with primary passage 28 for the flow of auxiliary fluid into or out of the modular group, and opening 83 of end plate 12a registers with primary passage 25 for the flow of gauge air form the modular assembly to a suitable pressure gauge (not shown). To receive connecting screws 13 (FIG. 1), openings 93 and 94 are provided at the opposite ends of each plate. It will be noted that one such opening (93) is threaded while the other (94) is unthreaded, permitting the parts to be joined by screws 13 extending in opposite directions from opposite ends of the stack.

The terminal clamping plates 12a and 12b are formed of steel or some other rigid material. Module sections 19 and 20 may also be formed of metal although a rigid plastic capable of being injection molded, such as modified polyphenylene oxide (marketed under the designation Norye 731 by General Electric Company, New York), has been found particularly suitable. Because of the distinctive configuration of the module sections, all of the passages may be formed during the injection molding process. The result is a structure of relatively few parts which may be easily and inexpensively manufactured and which, when fully assembled, provide a valve assembly adapted to perform multiple functions for a plurality of dental handpieces.

While in the foregoing I have disclosed an embodiment of the invention in considerable detail for purposes of illustration, it will be understood by those skilled in the art that many of these details may be varied without departing from the spirit and scope of the invention.

I claim:

1. A modular selector valve assembly for controlling fluid flow for a plurality of dental handpieces, said assembly comprising a plurality of substantially identical modules arranged in series and each having a pair of parallel planar outer side faces and being oriented in side-by-side relation, each module having an arrangement of transversely-extending main flow passages with corresponding passages of the respective modules being in axial alignment, each module being divided along a plane parallel with said outer side faces into a valve section and a control section, said sections of each module thereby being provided with inner side faces disposed in side-by-side relation to each other, said valve section having a plurality of valve passages extending transversely therethrough and parallel with said main passages, said control section having a plurality of transverse control passages extending transversely therethrough and also parallel with said main passages, said outer side face of said control section being provided with at least one open-sided control channel communicating with all of said control passages and said outer face of said valve section having a plurality of open-sided connecting channels joining pairs of said valve passages, passage means provided by said control section and communicating with said control channel for conveying pilot air to and from said control channel and control passages, passage means provided by each valve section adapted to communicate with a dental handpiece and being in flow communication with certain valve passages of said pairs of valve passages, a first flexible gasket imposed between the sections of each module, said first gasket having openings aligned with said main passages and being flexible into and out of engagement with portions of said inner face of said valve section about said valve passages to open and close said passages in response to changes in the pressure of pilot air in said control passages of said control section, a second flexible gasket interposed between and engaging the outer faces of the control and valve sections of successive modules of said series, each second gasket having openings aligned with said main passages and having imperforate portions sealing the open sides of said control and valve channels, and means securing said modules and gaskets together.

2. The selector valve assembly of claim 1 in which said first and second gaskets are substantially identical.

3. The selector valve assembly of claim 1 in which said control and valve sections are molded of rigid plastic material.

4. The selector valve assembly of claim 1 in which said last-mentioned means comprises rigid terminal clamping plates disposed at opposite ends of the series of modules, and means connecting said clamping plates for securing all of the modules of said series together.

5. The selector valve assembly of claim 4 in which said terminal clamping plates are substantially identical.

6. The selector valve assembly of claim 5 in which said identical clamping plates are reversely-oriented relative to each other, each plate having a non-symmetrical arrangement of openings of a number less than the total number of main flow passages through said modules, all of said openings in each plate being in register with main flow passages through said modules but certain of the openings of each plate being out of register with the openings of the other reversely-oriented plate.

7. A module for a selector valve assembly for use in controlling the flow of drive air, chip air and other fluids to dental handpieces, said module comprising a block having a pair of parallel outer side faces and an arrangement of main flow passages extending transversely therethrough, said module being divided along a plane parallel with said outer side faces into a valve section and a control section, said sections having inner side faces extending along said plane of division, said valve section having a plurality of transverse valve passages extending therethrough and parallel with said main passages, said control section having a plurality of transverse control passages extending therethrough and also parallel with said main passages, said outer side faces of said control section being provided with at least one open-sided control channel communicating with all of said control passages, said outer face of said valve section having a plurality of open-sided connecting channels joining pairs of said valve passages, passage means provided by said control section for conveying pilot air to and from said control channel, passage means provided by said valve section for directing fluids from certain valve passages of said pairs of valve passages for use by a dental handpiece, a first flexible gasket interposed between said sections and having openings aligned with said main passages, said first gasket being flexible into and out of engagement with portions of said inner face of said valve section about said valve passages to open and close said passages in response to changes in the pressure of pilot air in the control passages of said control section, and a second flexible gasket engaging one of the outer faces of said control and valve sections, said second gasket having openings aligned with said main passages and having imperforate portions sealing the open sides of the channels of said one of said control and valve sections.

8. The module of claim 7 in which a third flexible gasket engages the outer face of the other of said control and valve sections, said third gasket having openings aligned with said main passages and having imperforate portions sealing the open sides of the channels of the other of said control and valve sections.

9. The module of claim 7 in which said first and second gaskets are substantially identical.

10. The module of claim 7 in which said valve and control sections are injection molded from rigid plastic material.

11. The module of claim 10 in which all of said channels are molded into said valve and control sections.

* * * * *